United States Patent
Thrippleton

(10) Patent No.: US 9,297,037 B2
(45) Date of Patent: Mar. 29, 2016

(54) CLEARANCE BUFFER

(75) Inventor: Ian Thrippleton, Kaarst (DE)

(73) Assignee: MIACOM DIAGNOSTICS GMBH, Duesseldorf (DE)

(*) Notice: Subject to any disclaimer, the term of this patent is extended or adjusted under 35 U.S.C. 154(b) by 423 days.

(21) Appl. No.: 13/823,350

(22) PCT Filed: Sep. 14, 2011

(86) PCT No.: PCT/EP2011/065963
§ 371 (c)(1),
(2), (4) Date: Aug. 25, 2013

(87) PCT Pub. No.: WO2012/035076
PCT Pub. Date: Mar. 22, 2012

(65) Prior Publication Data
US 2014/0154678 A1    Jun. 5, 2014

(30) Foreign Application Priority Data
Sep. 14, 2010 (EP) ................... 10176697

(51) Int. Cl.
*C12Q 1/68* (2006.01)
*C07H 21/00* (2006.01)
*G01N 1/34* (2006.01)

(52) U.S. Cl.
CPC ............ *C12Q 1/6841* (2013.01); *C12Q 1/6806* (2013.01); *C12Q 1/6832* (2013.01)

(58) Field of Classification Search
CPC ............ C07H 21/00; C12Q 1/68; G01N 1/34
See application file for complete search history.

(56) References Cited

FOREIGN PATENT DOCUMENTS

| WO | 96/31626 A1 | 10/1996 |
|---|---|---|
| WO | 2009/058814 A1 | 5/2009 |
| WO | 2010/086099 A1 | 8/2010 |

OTHER PUBLICATIONS

Tajbakhsh Saeed et al: "Detection of Pseudomonas aeruginosa in sputum samples by modified fluorescent in situ hybridization", in: African Journal of Biotechnology, vol. 7, No. 5, Mar. 1, 2008, pp. 553-556.

Hogardt M et al: "Specific and rapid detection by fluorescent in situ hybridization of bacteria in clinical samples obtained from cystic fibrosis patients", in: Journal of Clinical Microbiology, vol. 38, No. 2, Feb. 1, 2000, pp. 818-825.

*Primary Examiner* — Ethan C Whisenant
(74) *Attorney, Agent, or Firm* — Joyce von Natzmer; Agris & von Natzmer LLP

(57) ABSTRACT

The invention concerns a composition comprising TCEP, biotin and dextran suitable for liquefying a viscous biological sample. The composition according to the invention can be used in diagnostic methods, preferably for use in diagnosis of an infection with a micro-organism, more preferably for use in diagnosis of HCAP.

24 Claims, 4 Drawing Sheets

CLEARANCE BUFFER

Figure 1:
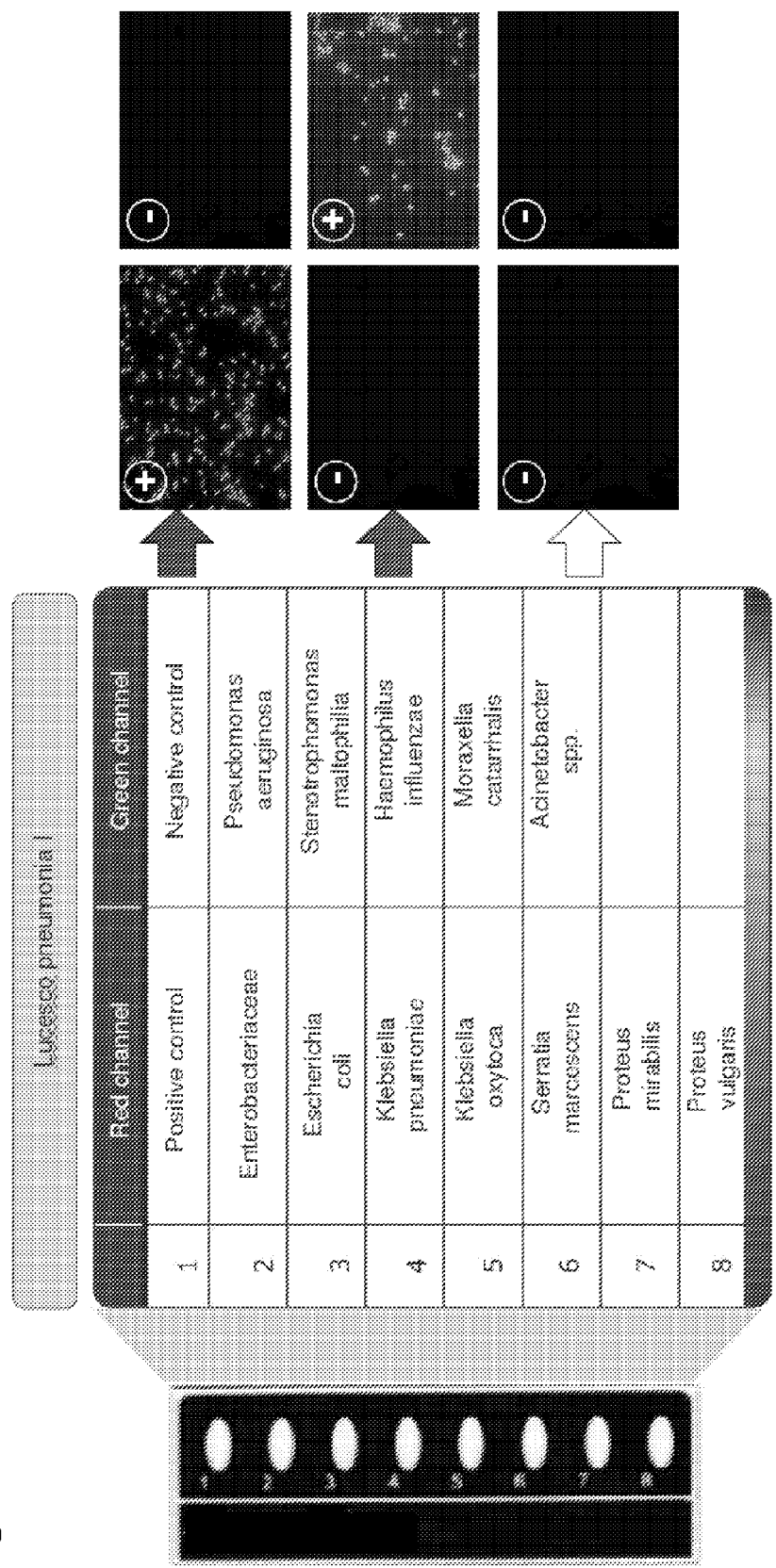

This is the U.S. national stage of International application PCT/EP2011/065963, filed Sep. 14, 2011 designating the United States and claiming priority to European application EP 10176697.0, filed Sep. 14, 2010.

Subject of the present invention is a composition comprising TCEP, biotin and dextran suitable for liquefying a viscous biological sample.

There is a dire need for rapid diagnosis of infectious diseases to reduce morbidity and mortality due to bacterial, viral, fungal and parasitical infections. Speed of diagnosis may be achieved if it is possible to analyse directly in the infected specimen. The mucous immune system is amongst the first line of defence of a body's immune system. A large part of the infections can therefore be detected in mucous secretions. These secretions can be viscous to semi solid and are thus difficult to handle. Preparation for laboratory analysis such as by immunochemistry, microscopy, fluorescence microscopy, molecular biology techniques in their entirety or any other method well known in the art is tedious and hampered by enzyme inhibitors, auto-fluorescent particles and poor signal to noise ratios. Even simple physical handling with pipettes proves cumbersome. Laboratories have therefore tried to find ways of liquefying sample.

Current state of the art methods are to liquefy by shaking vigorously with glass beads, reducing disulfide bonds readily present in mucous proteins with Sulphur reducing compounds such as Dithioerytrol (DTT) or other mercaptans components well known in the art. DTT is highly prone to oxidation via atmospheric oxygen and other mercaptans in addition render odours unpleasant or toxic. TCEP (tris(2-carboxyethyl)phosphine)) is reported as a substitute for DTT, however, TCEP reduces fluorescence in proteins, its presence in fluorescence assay might also be reduced.

However, Rhee and Burke demonstrated that TCEP stabilises RNA. The effect should be particularly poignant in ribosomal RNA. The application of TCEP in an in-situ hybridisation should alter the hybridisation conditions significantly.

In the present invention, it was surprisingly found that the hybridisation condition as described in EP 2 097 541 could remain unchanged. TCEP had no impact on the either Fluorophores used in this assay and the background was reduced as expected. A further reduction of background and autofluorescence was achieved by the addition of biotin combined with Dextran (dextran sulphate), buffered at a pH>8, in particular at a pH in the range of 8 to 10.

To those knowledgeable in the art, the effect of Dextran is to increase the apparent molar concentration of components in an aqueous solution, it was therefore surprising to find its background and auto-fluorescence reducing activity, especially in combination with biotin. It was further surprising to see the ease and speed with which even highly viscous sputa could be liquefied. Only 5 to 30 seconds of mild shaking was sufficient and no glass beads or vigorous vortexing as in standard procedures well known in the art was required. The method may be applied to all bodily secretions from nose, ear, eyes, mouth, respiratory tract, vagina, digestive tract, as well as wounds and catheters.

In a first aspect, the composition of the present invention (also termed "clearance buffer" or "CB") was devised containing TCEP in concentrations between 0.1 and 10 mM; Biotin in concentrations between 0.08 and 80 µM; dextran (in particular dextran sulphate) in concentrations between 0.01 and 10% (w/v), buffered at a pH between 7 and 10, wherein a buffer substance may be provided in concentrations between 10 and 100 mM. In a preferred embodiment the concentration was 1 and 5% (w/v) dextran (in particular dextran sulphate), 0.5 and 1.5 µM Biotin and between 1 and 3 mM TCEP, buffered at a pH between 7 and 10, for instance with a Tris buffer, wherein the buffer may be provided in concentrations between 30 and 70 mM. In the most preferred embodiment the concentration was about 2 mM TCEP, about 0.8 µM Biotin and about 2% dextran (in particular dextran sulphate) buffered with a pH of about 9.5, for instance with about 50 mM Tris buffer.

It simultaneously liquefies the sample and suppresses the auto-fluorescence, allowing the usage of DNA-beacons to directly identify pathogen in sputum samples. The clearance buffer (CB) was integrated into the bbFISH Method in the preparation step before the heat-fixation. All components therefore remain on the slide and are present during the hybridisation process and would therefore compromise a successful hybridisation.

The composition of the present invention (clearance buffer CB) can for instance be employed in the following exemplary protocol: CB can is added to a sample (1:1) and placed on a shaker for 5 minutes. 10 µl of liquefied sputum is placed on each field and air-dried at 52° C. Subsequently, a DNA-beacon-panel (see, for instance, the Example) was applied using the standard bbFISH procedure. Including sample preparation, the total turn-around time is less than 45 minutes.

Yet another aspect of the present invention is the composition described herein for use in diagnosis, preferably for use in diagnosis of an infection with a micro-organism, more preferably for use in diagnosis of HCAP. The micro-organism may be a micro-organism as described herein. Also a combination of micro-organisms, as described herein, may be diagnosed.

Yet another aspect of the present invention a method for the detection of a target nucleic acid sequence in a biological sample, comprising the steps
  (a) contacting the sample with a composition of the present invention, under conditions suitable for liquefying the sample,
  (b) contacting the sample of (a) with a hybridisation probe, in particular a hybridisation probe specific for rRNA in a micro-organism, such as a bacterium, wherein the probe carries a detectable label, and
  (c) detecting the presence of the target nucleic acid sequence in the sample of (b).

A further aspect is a method for the detection of a micro-organism in a biological sample, wherein the micro-organism comprises a target sequence, said method comprising the steps
  (a) contacting the sample with a composition of the present invention, under conditions suitable for liquefying the sample,
  (b) contacting the sample of (a) with a hybridisation probe, in particular a hybridisation probe specific for rRNA in a micro-organism, such as a bacterium, wherein the probe carries a detectable label, and
  (c) identifying the micro-organism by the presence of the target nucleic acid sequence in the sample of (b).

Conditions suitable for liquefying the sample may include mixing the sample and the composition. Also included may be incubating the sample and the composition for 3 to 120 seconds (preferably 3 to 60, 5 to 60 or 5 to 30 seconds) at room temperature (for instance, at a temperature selected from 18° C. to 25° C.). The conditions suitable for liquefying may include mild shaking for 3 to 120 seconds (preferably 3 to 60, 5 to 60 or 5 to 30 seconds).

The micro-organism may be selected from bacteria, yeasts and moulds, in particular from Gram positive or/and Gram negative bacteria. Also preferred is a micro-organism selected from the micro-organisms described in the Example. In the method(s) of the present invention, a combination of micro-organisms may be detected, for instance a combination consisting of Enterobacteriaceae, *Escherichia coli, Klebsiella pneumonia, Klebsiella oxytoca, Serratia marcescens, Proteus mirabilis, Proteus vulgaris, Pseudomonas aeruginosa, Stenotrophomonas maltophila, Haemophilus influenzae, Moraxella catarrhalis, Acetinobacter* ssp. Also a sub-combination comprising 2, 3, 4, 5, 6, 7, 8, 9, 10, or 11 species selected from the specific combination described herein may be detected.

In the method(s) of the present invention, the label can be a luminescent label, in particular a fluorescent label. Suitable labels are for instance described in EP 2 097 541, the disclosure of which in included herein by reference.

In the method(s) of the present invention, the hybridisation probe may be a probe comprising a molecular beacon. Suitable molecular beacons are described in EP 2 097 541, the disclosure of which in included herein by reference. The method(s) include conditions suitable for hybridisation of the probe with the target nucleic acid. Suitable conditions are disclosed in EP 2 097 541, the disclosure of which in included herein by reference.

In the method of the present invention, detection may be performed by fluorescence in-situ hybridisation (FISH). Suitable conditions are for instance described in EP 2 097 541, the disclosure of which is included herein be reference.

In the method(s) of the present invention, the sample may be a viscous or a highly viscous sample. The sample may be a bodily secretion selected from secretions from nose, ear, eyes, mouth, respiratory tract, vagina, digestive tract, wounds and catheters. The sample may also be a sputum sample.

The method(s) of the present invention may be a method of diagnosis, in particular a method of diagnosis of an infection with a micro-organism, more preferably of HCAP. The micro-organism may be a micro-organism as described herein. Also a combination of micro-organisms, as described herein, may be diagnosed.

Another aspect of the present invention is the use of the composition of the present invention described herein in the detection of a target nucleic acid sequence in a biological sample or/and in the identification of a micro-organism in a biological sample. Conditions may be used as described herein for the method(s) of the present invention. The biological sample may be a sample as described herein. Detection may be performed by FISH. A probe may be used as described herein.

REFERENCES

Steven S. Rhee and Donald H. Burke Tris(2-carboxyethyl) phosphine stabilization of RNA: comparison with dithiothreitol for use with nucleic acid and thiophosphoryl chemistry Analytical Biochemistry, Vol. 325(1), 1 Feb. 2004, Pages 137-143

Masterton R. G., Galloway A., et al. Guidelines for the management of hospital-acquired pneumonia in the UK: Report of the Working Party on Hospital-Acquired Pneumonia of the British Society for Antimicrobial Chemotherapy. JAC 2008; 62, 5-34

Baughman R. P., Tapson V., McIvor A., The Diagnosis an Treatment Challenges in Nosocomial Pneumonia. Diagn Microbiol Infect Dis 1999, 33, 131-139

The invention is illustrated by the following example and figures.

FIGURE LEGENDS

FIG. 1: Beacon compilation and example of a typical readout (upper panel: positive control; middle panel: positive identification of *H. influenzae*; lower panel: negative)

Figure 2:
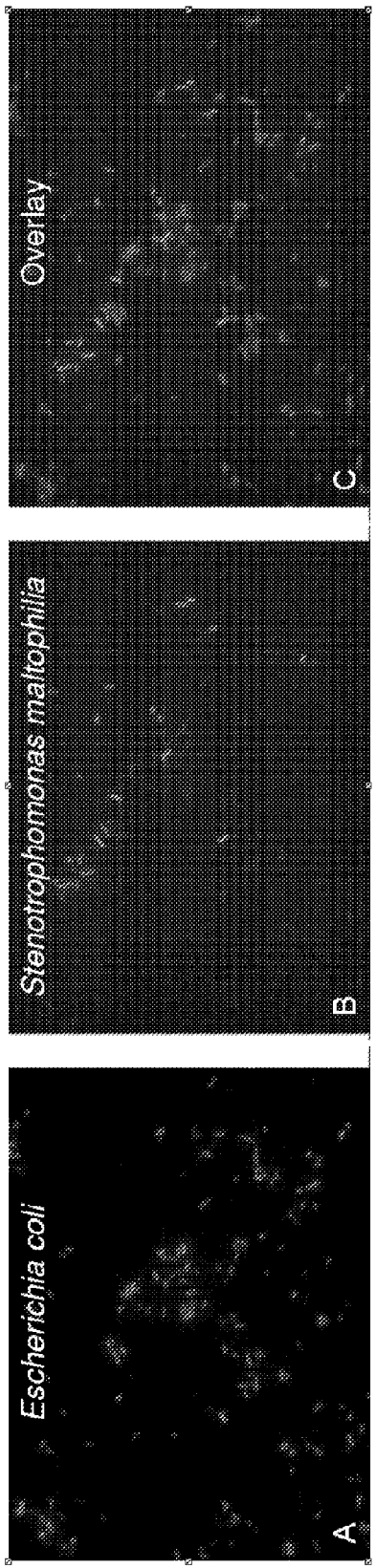

FIG. 2: Example of a spiked mixed infection showing: A *E. coli* using the *E. coli*-beacon; B *S. maltophilia* using the *S. maltophilia*-beacon; A & B were taken from the same visual field; C Overlay picture of both probes. Pictures taken at 1000× magnification on an Olympus fluorescence microscope BX 41.

Figure 3:
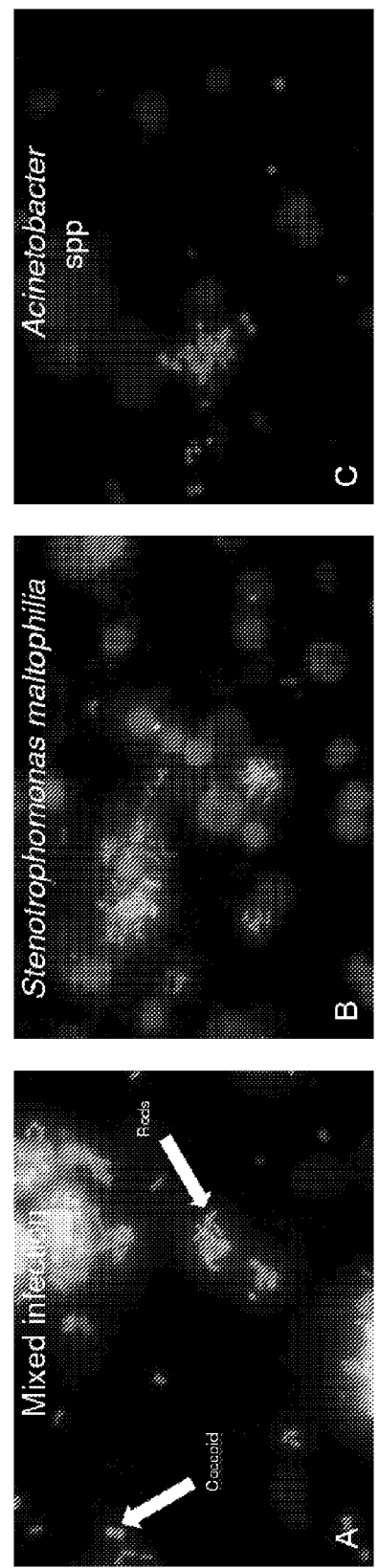

FIG. 3: Example of a sputum specimen with a mixed infection: A Positive control showing both rods and coccobacilli; B The rods were identified using the *S. maltophilia*-specific beacon; C The coccobacilli were identified using the *Acinetobacter* spp.-specific beacon. Magnification 1000× on an Olympus fluorescence microscope BX 41.

Figure 4:
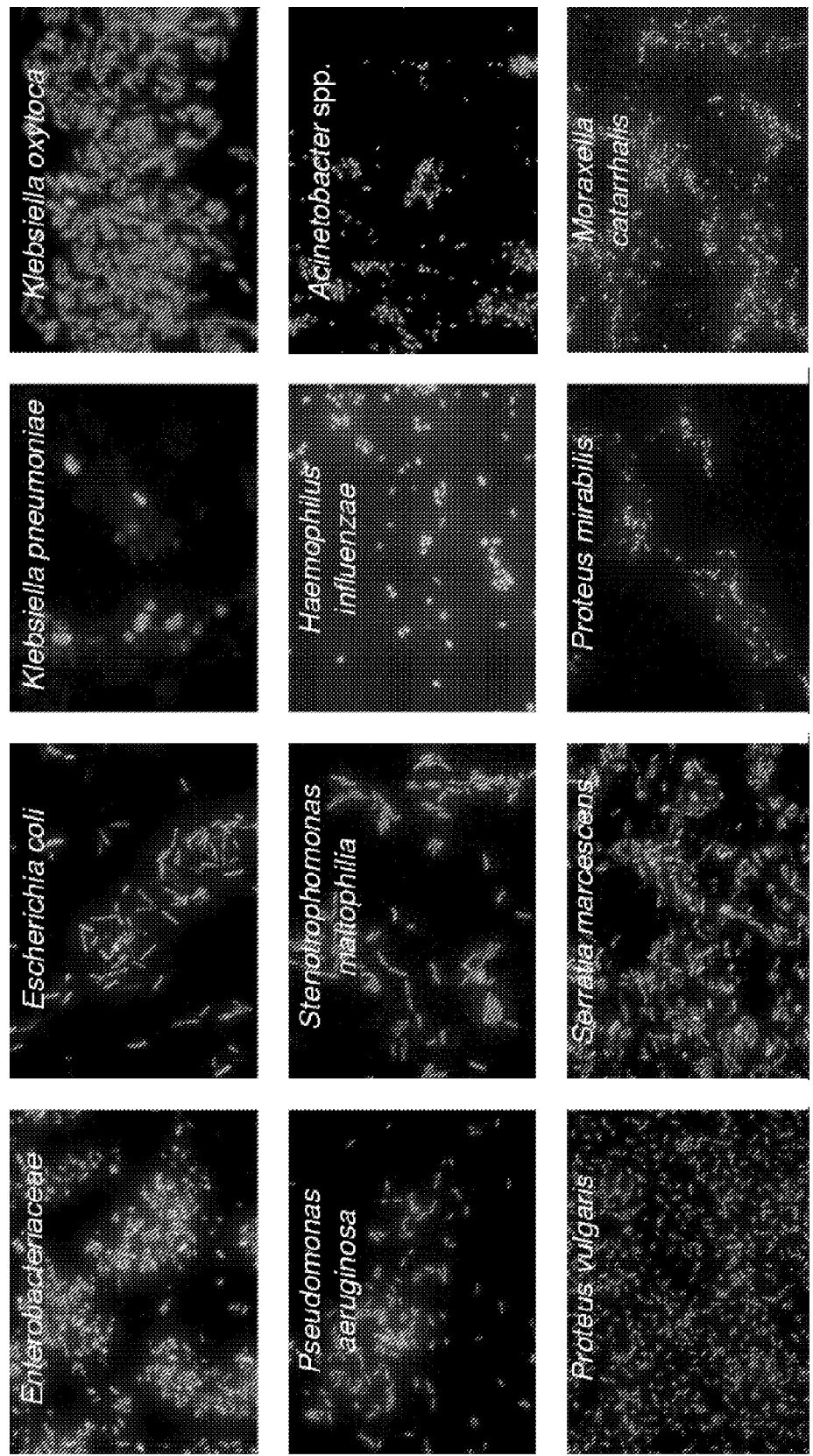

FIG. 4: Targeted organisms: ATCC-strains taken at 1000× magnification with Olympus BX 41 ($\lambda_{Exc.}$=494 nm; $\lambda_{Em.}$=520 nm or $\lambda_{Exc.}$=554 nm; $\lambda_{Em.}$=576 nm) and hybridised with respective species specific beacons.

Figure 5:
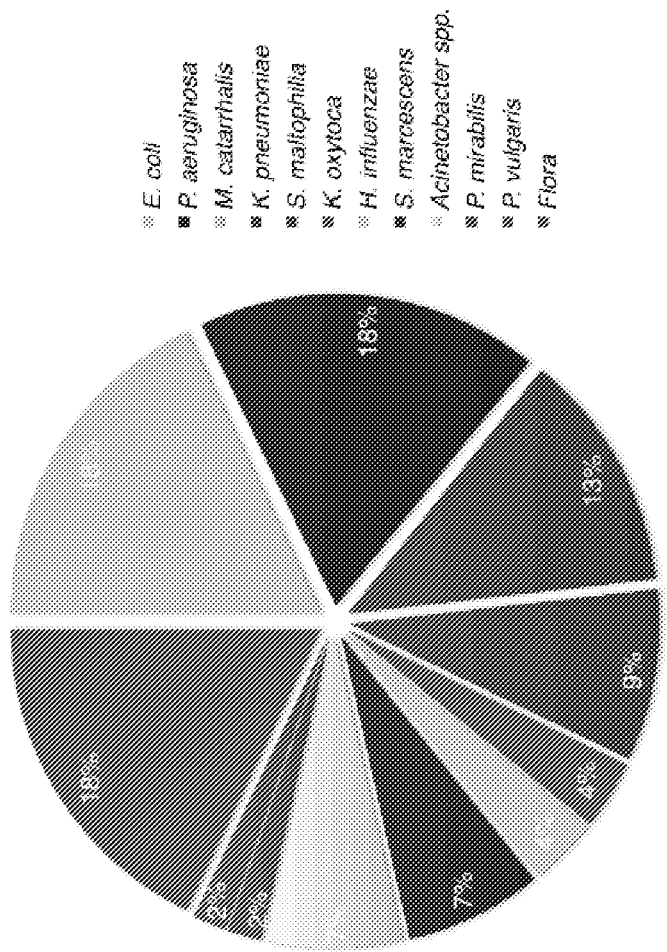

FIG. 5: Frequency of identification

EXAMPLE

Rapid Identification of Pathogens Causing Health Care Associated Pneumonia (HCAP) Directly in Respiratory Secretions from ICU Patients by Beacon-Based FISH (bbFISH)

Introduction:

Hospital-acquired pneumonia (HAP) is the most common healthcare-associated infection contributing to 50% of respective deaths (Masterton et al., 2008, Baughman et al., 1999). Rapid initiation of antibiotic therapy is essential in reducing mortality and morbidity as well as hospital costs. A rapid test, directly from respiratory specimen, to identify a possible causative organism could lead to targeted antibiotic therapy which reduces the development of antimicrobial resistance.

Material and Methods:

Study:

This study was performed to evaluate the lucesco pneumonia I assay (miacom diagnostics GmbH) to detect Gram-negative bacteria (causing HAP in an interdisciplinary surgical ICU. Between July and August 2010, 53 respiratory specimen from 53 ICU patients were selected by a modified Q-Score, analyzed via bbFISH technology and compared to culture results. No selection was made with respect to sex and age. The Q-Score was defined as: 1. occasional leukocyte and detritus, 2. few leukocytes, 3. moderate leukocytes, 4. high leukocytes. Only specimen achieving a Q-score of 3 were included.

Identification Via Culture:

All specimen were plated on MacConkey-, Columbia- and Chocolate-agar plates and incubated at 36° C. over night. All pathogens were identified by routine microbiological methods.

Identification Via bbFISH:

Highly viscous samples were liquefied and prepared for bbFISH by adding a clearance buffer (CB) containing tris(2-carboxyethyl)phosphine as a mucolytic reagent and biotin and dextran sulphate as an auto-fluorescence-suppressor.

10 µl aliquots were placed on each field of an 8-field microscope slide and dried on a 52° C. hotplate. After drying, 10 µl lysis-buffer was added to each field with an 8-channel multipipette and left to dry. Thereafter the slide was placed in an 96% ethanol bath for 5 minutes. After drying, hybridisation solutions were placed on each field. The slide was then covered with a hybridisation lid and incubated at 52° C. for 10 minutes. Subsequently the slide was immersed in stop-buffer for 1 min., dipped in ethanol, dried, mounted and read under a fluorescence microscope at 1000× magnification. The filters used were: A) max. $\lambda_{ex}$=494 nm and B) max. $\lambda_{ex}$=554 nm.

Results

- The clearance buffer allowed simple and efficient handling of highly viscous respiratory specimen
- The total turn-around time for one sample proved to be 40 minutes, including sample preparation
- Out of the twelve detectable pathogens, eleven occurred in this study
- In 3 cases pathogens were present, which are not part of the panel
- In 1 case bbFISH failed to detect pathogens detected by culture
- In 51 cases bbFISH was able to detect pathogens detected by culture
- bbFISH was able to detect a mixed infection and allow the determination of the numerically predominant organism

TABLE 1

Calculated sensitivity and specificity of the lucesco pneumonia assay. Statistical analysis

| | |
|---|---|
| Sensitivity | 97% |
| Specificity | 93% |
| p value | 0.077 |
| n | 53 |

TABLE 2

Comparison of culture results to those of the HAP-Panel

| Patient number | Culture (predominant pathogen) | bbFISH |
|---|---|---|
| 23027 | M. catarrhalis, E. cloacae | H. influenzae |
| 31225 | Flora | Flora |
| 22939 | S. maltophilia | S. maltophilia |
| 22940 | K. ornithinolytica | P. aeruginosa, K. oxytoca |
| 31108 | S. marcescens | S. marcescens |
| 31226 | Flora | Flora |
| 23004 | Gram-positive cocci | no Gram-negative bacteria |
| 22941 | Candida | no Gram-negative bacteria |
| 23005 | E. coli | E. coli, P. aeruginosa |
| 22942 | E. cloacae, P. aeruginosa | E. coli |
| 31223 | Flora | no Gram-negative bacteria |
| 23811 | P. aeruginosa | P. aeruginosa, S. maltophilia, S. marcescens |
| 32374 | Flora | Flora |
| 32309 | Flora | Flora |
| 32371 | Gram-positive cocci | no Gram-negative bacteria |
| 32372 | E. coli | E. coli, K. pneumoniae, P. vulgaris |
| 32367 | P. aeruginosa | P. aeruginosa |
| 32370 | P. aeruginosa | P. aeruginosa |
| 32312 | P. aeruginosa, S. marcescens | S. marcescens |
| 32310 | Gram-positive cocci | no Gram-negative bacteria |
| 32311 | Proteus spp. | S. marcescens |
| 32661 | Flora | E. coli, Acinetobacter spp. |
| 24112 | no growth | no Gram-negative bacteria |
| 24007 | Gram-pos. cocci, S. maltophilia, K. pneumoniae, E. coli | E. coli, S. maltophilia, K. oxytoca |
| 24624 | no growth | no Gram-negative bacteria |
| 24700 | K. pneumoniae, Proteus spp., Gram-positive cocci | E. coli, K. pneumoniae |
| 33427 | E. coli | E. coli |
| 33416 | H. influenzae | H. influenzae |
| 33425 | Enterobacteriacea | Enterobacteriaceae |
| 33629 | Flora | Flora |
| 24825 | Flora | Flora |
| 24918 | E. coli | E. coli, K. pneumophilia |
| 24823 | E. coli | E. coli, K. pneumophilia, P. mirabilis |
| 24829 | no growth | no Gram-negative bacteria |
| 24830 | S. maltophilia, A. baumannii | S. maltophilia, Acinetobacter spp. |
| 25491 | P. aeruginosa | P. aeruginosa |
| 25493 | Gram-positive cocci | no Gram-negative bacteria |
| 25538 | P. aeruginosa, Gram-positive cocci | P. aeruginosa |
| 34493 | E. coli | E. coli, K. pneumoniae |
| 34492 | Flora | no Gram-negative bacteria |
| 25794 | P. aeruginosa | P. aeruginosa |
| 25745 | P. aeruginosa | P. aeruginosa |
| 25680 | no growth | no Gram-negative bacteria |
| 25673 | no growth | no Gram-negative bacteria |
| 25670 | K. pneumoniae | K. pneumoniae |
| 25820 | E. coli, K. pneumoniae | E. coli, K. pneumoniae |
| 35708 | P. aeruginosa | P. aeruginosa, Acinetobacter spp. |

TABLE 2-continued

Comparison of culture results to those of the HAP-Panel

| Patient number | Culture (predominant pathogen) | bbFISH |
|---|---|---|
| 35581 | Flora | Flora |
| 26392 | S. maltophilia, Enterobacteriaceae | S. maltophilia, Acinetobacter spp. |
| 26396 | Flora | Flora |
| 26398 | Candida | no Gram-negative bacteria |
| 26404 | Flora | no Gram-negative bacteria |
| 26403 | Flora | Flora |

Discussion

The TCEP breaks the disulfide bonds in proteins, significantly reducing the viscosity of sputum.

Briefly (5-60 sec) shaking the vial mildly is sufficient to liquefy even semi-solid sputa.

Due to its low susceptibility to oxidation TCEP does not need to be freshly made on a daily basis.

Although TCEP is a strong reducer, the liquefied specimen is not a completely homogeneous solution. Small mucoid particles still remain and are visible under the microscope. The particles may contain any number of organisms which would only result in one colony on an agar plate, rendering a quantitative evaluation and comparison to colony count questionable. The qualitative and quantitative evaluation and correlation to clinical data will be subject of a further investigation.

The application of CB allows a safe and rapid specimen preparation in routine handling, without reducing the number of viable organisms. This in turn gives an authentic estimate of the respective numbers of the bacteria present in the sampled respiratory tract before selective growth of rapid growing bacteria masks the true predominant pathogen.

The addition of both biotin and dextran sulphate ensures both the reduction of the background fluorescence by its mucolytic action, as well as increasing the fluorescent signal due to the concentrating factor of the biotin and dextran sulphate.

The turn-around time of 40 minutes allows a very timely reporting of the pathogens in respiratory specimen.

CONCLUSION bbFISH is easy to perform in a routine laboratory and proved to be a reliable method for the rapid detection of pathogens causing nosocomial pneumonia. The technology enables correct identification of pathogens directly from respiratory specimen such as bronchial and tracheal secretions or sputa, without cultivation or amplification, within 40 minutes.

The invention claimed is:

1. Liquid composition comprising:
   0.1 mM to 10 mM TCEP,
   0.08 pM to 80 pM biotin, and
   0.01% w/v to 10% w/v of dextran in an aqueous medium at pH 7 to 10.

2. Composition according to claim 1, comprising:
   1 mM to 3 mM TCEP,
   0.5 pM to 1.5 pM biotin, and
   1% w/v to 5% w/v of dextran.

3. Composition according to claim 2, comprising:
   about 2 mM TCEP,
   about 0.8 pM biotin, and
   about 2% w/v of dextran.

4. Composition according to claim 1, wherein a buffer substance is present in a concentration of 10 to 100 mM.

5. Composition according to claim 4, wherein the buffer substance is present in a concentration of 30 to 70 mM.

6. Composition according to claim 5, wherein the buffer substance is present in a concentration of about 50 mM.

7. Composition according to claim 1, wherein the composition is buffered with TRIS.

8. Composition according to claim 1, wherein the pH is 8 to 10.

9. Composition according to claim 1, wherein the pH is about 9.5.

10. A method for detecting a micro-organism in a biological sample, wherein the micro-organism comprises a target sequence, wherein said method comprises
    (a) contacting the sample with a composition of claim 1, under conditions suitable for liquefying the sample,
    (b) contacting the sample of (a) with a hybridisation probe specific for rRNA in a micro-organism, wherein the probe carries a detectable label, under conditions suitable for hybridisation of the probe with the target nucleic acid, and
    (c) identifying the micro-organism by the presence of the target nucleic acid sequence in the sample of (b).

11. A method for detecting a target nucleic acid sequence in a biological sample, comprising
    (a) contacting the sample with a composition of claim 1, under conditions suitable for liquefying the sample,
    (b) contacting the sample of (a) with a hybridisation probe specific for rRNA in a micro-organism, wherein the probe carries a detectable label, under conditions suitable for hybridisation of the probe with the target nucleic acid, and
    (c) detecting the presence of the target nucleic acid sequence in the sample of (b).

12. The method of claim 10, wherein the micro-organism is detected and healthcare associated pneumonia (HCAP) is diagnosed.

13. The method of claim 11, wherein the label is a luminescent label.

14. The method of claim 11, wherein the probe comprises a molecular beacon.

15. The method of claim 11, wherein detection is performed by fluorescence in-situ hybridisation (FISH).

16. The method of claim 11, wherein the sample is viscous.

17. The method of claim 11, wherein the sample comprises a bodily secretion selected from secretions from nose, ear, eyes, respiratory tract, vagina, digestive tract, wounds and catheters.

18. The method of claim 10, wherein the label is a luminescent label.

19. The method of claim 10, wherein the probe comprises a molecular beacon.

20. The method of claim 10, wherein the sample is viscous.

21. The method of claim 11, wherein the micro-organism is a bacterium.

22. The method of claim 10, wherein the micro-organism is a bacterium.

23. The method of claim 13, wherein the luminescent label is a fluorescent label.

24. The method of claim 18, wherein the luminescent label is a fluorescent label.

* * * * *